US012655098B2

(12) United States Patent
Koerfer et al.

(10) Patent No.: US 12,655,098 B2
(45) Date of Patent: Jun. 16, 2026

(54) D,L-METHIONINE WITH AN OPTIMIZED PARTICLE SIZE DISTRIBUTION

(71) Applicant: Evonik Operations GmbH, Essen (DE)

(72) Inventors: Martin Koerfer; Hans-Joachim Hasselbach, Gelnhausen (DE); Stefan Reichert, Frankfurt (DE); Mauricio Antezana, Santa Cruz (BO); Antje Hansmeier, Frankfurt am Main (DE)

(73) Assignee: Evonik Operations GmbH, Essen (DE)

( * ) Notice: Subject to any disclaimer, the term of this patent is extended or adjusted under 35 U.S.C. 154(b) by 559 days.

(21) Appl. No.: 18/248,667

(22) PCT Filed: Oct. 11, 2021

(86) PCT No.: PCT/EP2021/078010

§ 371 (c)(1),
(2) Date: Apr. 11, 2023

(87) PCT Pub. No.: WO2022/078940

PCT Pub. Date: Apr. 21, 2022

(65) Prior Publication Data

US 2023/0391720 A1 Dec. 7, 2023

(30) Foreign Application Priority Data

Oct. 13, 2020 (EP) ..................................... 20201501

(51) Int. Cl.
*C07C 323/58* (2006.01)

(52) U.S. Cl.
CPC .................................. *C07C 323/58* (2013.01)

(58) Field of Classification Search
CPC ...................................................... C07C 323/58
See application file for complete search history.

(56) References Cited

U.S. PATENT DOCUMENTS

| | | | |
|---|---|---|---|
| 5,770,769 A | 6/1998 | Geiger et al. | |
| 9,260,732 B2 * | 2/2016 | Hong ...................... | C12P 13/12 |

(Continued)

FOREIGN PATENT DOCUMENTS

| | | |
|---|---|---|
| CN | 109682170 A | 4/2019 |
| CN | 110621657 A | 12/2019 |

(Continued)

OTHER PUBLICATIONS

International Search Report and Written Opinion issued Dec. 13, 2021 in PCT/EP2021/078010 filed on Oct. 11, 2021, 15 pages.

(Continued)

*Primary Examiner* — Yate' K Cutliff
(74) *Attorney, Agent, or Firm* — Oblon, McClelland, Maier & Neustadt, L.L.P.

(57) ABSTRACT

D,L-methionine may include, based on the total weight of the D,L-methionine, from 15 to less than 50 wt.-% of the D,L-methionine with a particle size from more than 0 to less 150 micrometers, from 50 to less than 90 wt.-% of the D,L-methionine with a particle size from more than 0 to less 300 micrometers, and from 30 to less than 80 wt.-% of the D,L-methionine with a particle size in the range between 63 and 300 micrometers. The D,L-methionine may have a bulk density of at least 710 kg/m³.

4 Claims, 1 Drawing Sheet

(56) References Cited

U.S. PATENT DOCUMENTS

| | | | | |
|---|---|---|---|---|
| 2009/0306426 | A1* | 12/2009 | Koizumi | ............... C07C 319/20 |
| | | | | 562/559 |
| 2015/0051421 | A1 | 2/2015 | Koerfer et al. | |
| 2018/0043281 | A1* | 2/2018 | Chen | .................... B01D 9/0013 |
| 2019/0112247 | A1 | 4/2019 | Clark et al. | |
| 2021/0087000 | A1 | 3/2021 | Koizumi et al. | |

FOREIGN PATENT DOCUMENTS

| | | | |
|---|---|---|---|
| CN | 109682170 B * | 7/2023 | ............... F26B 3/08 |
| EP | 2 133 329 A2 | 12/2009 | |
| EP | 3 246 310 A1 | 11/2017 | |
| JP | 2001-72656 A | 3/2001 | |
| SU | 1010423 A | 4/1983 | |
| WO | WO 2013/139562 A1 | 9/2013 | |

OTHER PUBLICATIONS

European Search Report issued Mar. 29, 2021 in European Application 20201501.2 filed on Oct. 13, 2020, 8 pages.

* cited by examiner

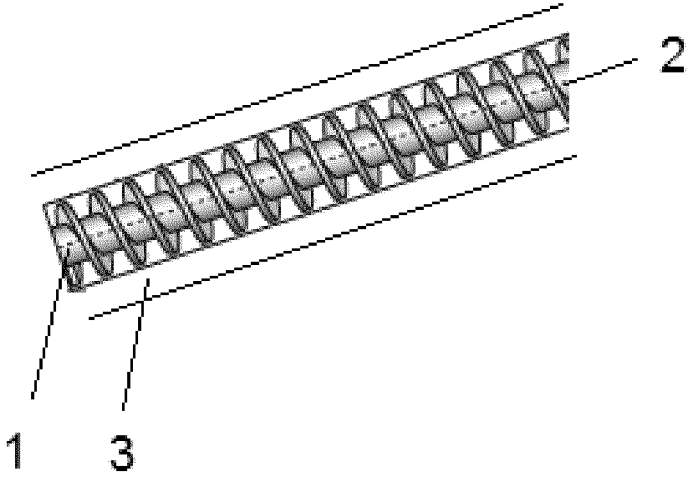

D,L-METHIONINE WITH AN OPTIMIZED PARTICLE SIZE DISTRIBUTION

CROSS-REFERENCE TO RELATED APPLICATIONS

The present application is the national stage of international application PCT/EP2021/078010, filed on Oct. 11, 2021, and claims the benefit of the filing date of European Appl. No. 20201501.2, filed on Oct. 13, 2020.

The present invention relates to a D,L-methionine with an optimized particle size distribution and a process for preparing said D,L-methionine with an improved particle size distribution.

According to the U.S. Pat. No. 5,770,769 D,L-methionine (in the following simply referred to as methionine) is prepared by reacting 3-methylthiopropionaldehyde with hydrogen cyanide, ammonia and carbon dioxide to give 5-(2-methylmercaptoethyl)-hydantoin, followed by the hydrolysis of the hydantoin in the presence of an inorganic base, typically potassium carbonate, to give a salt of methionine. Finally, said methionine salt is neutralized by blowing carbon dioxide through an aqueous solution of the methionine salt to give methionine, which precipitates from the solution. Finally, the thus obtained crude methionine is re-crystallized to improve purity, as described for example in US 2015/051421 A1. The thus obtained methionine has a bulk density of from 500 to 580 g/I only.

The term bulk density is synonym with the term bulk weight and denotes the density of a mixture of a particulate solid, the so-called bulk material, and a continuous fluid, typically air, which occupies the vacancies or hollows between the particles, per volume or in other words the mass of said mixture per volume. A high reproducible bulk density therefore allows the filling of a specific volume, e.g. the volume of a transport container or transport bag, with the highest possible amount of product. The bulk density of a product is therefore an important key figure in the production of organic compounds. Compared to the methionine density of 1.34 $g/cm^{-3}$ or 1,340 g/I, the process of US 2015/051421 A1 gives a rather low methionine bulk density of only 500 to 580 g/I.

When the solution of a methionine salt is neutralized and crystallized with carbon dioxide, the foaming phenomenon is a significant factor affecting the results of the neutralization and crystallization during the crystallization process. In most of the prior art, defoamers, flocculants and other additives are added during the crystallization process in order to avoid or reduce the foaming phenomenon. According to EP 3246310 A1, a part of these additives will attach to the surface of the methionine crystals and be brought out by the methionine crystals, while the rest remains in the mother liquor, and is recycled together with the mother liquor. According to EP 3246310 A1, the recycling of the later additives together the mother liquor will change the proportion of the additives in the mother liquor or will be deteriorated to unknown material due to the heat, thereby affecting the subsequent neutralization and crystallization process and increasing instability in the neutralization and crystallization process. Amongst others, this leads to methionine with a reduced bulk density. According to EP 3246310 A1, the problems of foam generation and of reduced bulk density are solved by using a DTB neutralization crystallizer having a gas phase neutralization section, the neutralization in the liquid phase, that is easy to generate a foaming phenomenon, is transferred to be carried out in a gas phase, so as to essentially eliminate the foaming problem in the neutralization process. Meanwhile, by controlling the oversaturation in the crystallization process, formation of crystal neclues is effectively controlled, thereby obtaining methionine with high bulk density. EP 2133329 A2 discloses a process for producing methionine, which comprises the steps of: hydrolyzing 5-[2-(methylthio)ethyl]imidazolidine-2,4-dione in the presence of a basic potassium compound in a non-stirred continuous first reaction tank, and heat-treating the reaction solution after hydrolysis in a second reaction tank. According to the process of EP 2133329 A2, a methionine with a higher bulk density can be produced.

In the process of WO 2013/139562 A1 methionine crystals are separated from the mother liquor by means of a solid/liquid separation step, for example using a vacuum belt filter or a centrifuge. In the next step, the methionine particles are dried in a steam treatment. Here, steam is directed onto the methionine containing filter cake at the end of the belt filter to vaporize the remaining mother liquor still adhering on the methionine particles. The thus obtained methionine has a bulk density of up to 650 g/I. Further experiments have shown that fine methionine particles (dust) are removed during the drying in the steam treatment. This is believed to affect the bulk density of the thus obtained methionine adversely.

The processes of the prior art give methionine with a bulk density, which is either far below a desired bulk density of 680 $kg/m^3$ or more, or only obtained by processes, which are rather sophisticated and not suitable on industrial scale. Therefore, it was still a problem to be solved to provide a methionine with an optimized particle size distribution, which provides the methionine with an increased bulk density.

According to the present invention this problem is solved by a D,L-methionine, comprising based on the total weight of the D,L-methionine from 15 to less than 50 wt.-% of the D,L-methionine with a particle size from more than 0 to less than 150 micrometer, from 50 to less than 90 wt.-% of the D,L-methionine with a particle size from more than 0 to less than 300 micrometer, and from 30 to less than 80 wt.-% of the D,L-methionine with a particle size in the range between 63 and 300 micrometer.

Said D,L-methionine has a bulk density of at least 710 $kg/m^3$.

Object of the present invention is therefore D,L-methionine, comprising based on the total weight of the D,L-methionine from 15 to less than 50 wt.-% of the D,L-methionine with a particle size from more than 0 to less than 150 micrometer, from 50 to less than 90 wt.-% of the D,L-methionine with a particle size from more than 0 to less than 300 micrometer, and from 30 to less than 80 wt.-% of the D,L-methionine with a particle size in the range between 63 and 300 micrometer, wherein the D,L-methionine has a bulk density of at least 710 $kg/m^3$.

Any one-sided open range is used in the context of the present invention to denote a range whose lower endpoint, which is not explicitly mentioned, is always larger than 0. This applies to any one-sided open range of a fraction given in weight percent (wt.-%) and to any one-sided open range of a particle size given in micrometer.

All weight percentages (wt.-%) used in the context of the present invention are always based on the total weight of methionine. Deviations from the explicitly mentioned weight percentages are encompassed by the scope of the present invention, provided that they still lead to the technical benefits of the present invention.

The D,L-methionine according to the present invention always has a bulk density of at least 710 kg/$m^3$ or even more than 740 kg/$m^3$, which is a significantly higher bulk density than in the prior art. The D,L-methionine according to the present invention can have a bulk density of up to 760 kg/$m^3$.

Preferably, the upper limit of the D,L-methionine with a particle size of more than 0 to less than 300 micrometer, is 70 wt.-%.

In an embodiment the D,L-methionine according to the present invention comprises from 50 to 70 wt.-% of the D,L-methionine with a particle size of more than 0 to less than 300 micrometer.

Preferably, the lower limit of the D,L-methionine with a particle size in the range between 63 and 300 micrometer is 30 wt.-%. It is further preferred that the upper limit of the methionine with a particle size in the range between 60 and 300 micrometer is 75 wt.-% In another embodiment the D,L-methionine according to the present invention comprises from 30 to 75 wt.-% of the D,L-methionine with a particle size in the range between 63 and 300 micrometer.

Preferably, the D,L-methionine according to the present invention comprises from 30 to 60 wt.-% or from 30 to 65 wt.-% of the D,L-methionine with a particle size in the range between 63 and 300 micrometer.

Preferably, the lower limit for the methionine according to the present invention with a particle of more than 0 to less than 150 micrometer, is 15 wt.-%.

Preferably, the D,L-methionine according to the present invention comprises

- from 15 to less than 50 wt.-% of the D,L-methionine with a particle size from more than 0 to less 150 micrometer,
- from 50 to less than 90 wt.-% or from 50 to 70 wt.-% of the D,L-methionine with a particle size of more than 0 to less than 300 micrometer, and
- from 30 to 75 wt.-% of the D,L-methionine with a particle size in the range between 63 and 300 micrometer.

Preferably, the D,L-methionine according to the present invention also comprises D,L-methionine with a particle size larger than 300 micrometer, for example from 300 to 500 micrometer, from 500 to 710 micrometer, from 710 to 1000 micrometer and optionally more than 1000 micrometer.

Preferably, the lower limit for the D,L-methionine with a particle size from 300 to 500 micrometer is 10 wt.-% and the upper limit for the D,L-methionine with a particle size from 300 to 500 micrometer is 45 or 50 wt.-%.

In a further embodiment of the D,L-methionine according to the present invention, the D,L-methionine also comprises from 10 to 45 or from 10 to 50 wt.-% of the D,L-methionine with a particle size from 300 to 500 micrometer.

Preferably, the D,L-methionine according to the present invention also comprises D,L-methionine with a particle size from 500 to 710 micrometer. Preferably, the lower limit for the D,L-methionine with a particle size from 500 to 710 micrometer is 1 wt.-% and the upper limit for the D,L-methionine with a particle size from 500 to 710 micrometer is 20 wt.-%.

In a further embodiment the D,L-methionine according to the present invention also comprises from 1 to 20 wt.-% of the D,L-methionine with a particle size from 500 to 710 micrometer.

Preferably, the D,L-methionine according to the present invention also comprises D,L-methionine with a particle size from 710 to 1000 micrometer. Preferably, the upper limit for the D,L-methionine with a particle size from 710 to 1000 micrometer is 10 wt.-%.

In yet another embodiment the D,L-methionine according to the present invention also comprises from more than 0 to 10 wt.-% of the D,L-methionine with a particle size from 710 to 1000 micrometer.

Preferably, the D,L-methionine according to the present invention also comprises D,L-methionine with a particle size of more than 1000 micrometer. Preferably, the upper limit for the D,L-methionine with a particle size of more than 1000 micrometer is 5 wt.-%, in particular 2 wt.-%.

In a further embodiment the D,L-methionine according to the present invention comprises up to 5 wt.-% of the D,L-methionine with a particle size of more than 1000 micrometer.

The D,L-methionine according to the present invention is not limited regarding specific amounts of the D,L-methionine with a particle of less than 32 micrometer, of the D,L-methionine with a particle size from 32 to 63 micrometer, of the D,L-methionine with a particle size from 63 to 100 micrometer, and of the D,L-methionine with a particle size from 100 to 150 micrometer, provided that the individual amounts of said particle size ranges meet the requirement that from 15 to less than 50 wt.-% of the D,L-methionine have a particle size from more than 0 to less 150 micrometer.

Notwithstanding it is preferred that the methionine according to the present invention comprises from more than 0 to 20 wt.-% of the methionine with a particle size of less than 32 micrometer, that the methionine according to the present invention comprises from more than 0 to 20 wt.-% of the methionine with a particle size in the range from 32 to 63 micrometer, that the methionine according to the present invention comprises from more than 0 to 10 wt.-% from the methionine with a particle size in the range from 63 to 100 micrometer, and/or that the methionine according to the present invention comprises from 5 to 15 wt.-% of the methionine with a particle size in the range from 100 to 150 micrometer.

In an embodiment the D,L-methionine according to the present invention comprises

- up to 10 wt.-% of the D,L-methionine with a particle size in the range between 63 and 100 micrometer,
- from 20 to 50 wt.-% of the D,L-methionine with a particle size from more than 0 to less than 150 micrometer,
- from 50 to 70 wt.-% of the D,L-methionine with a particle size from more than 0 to less than 300 micrometer,
- from 30 to 75 wt.-% of the D,L-methionine with a particle size in the range between 63 and 300 micrometer,
- from 10 to 65 wt.-% of the D,L-methionine with a particle size in the range between 300 to 500 micrometer,
- from 1 to 20 wt.-% of the D,L-methionine with a particle size in the range between 500 to 710 micrometer,
- from more than 0 to 10 wt.-% of the D,L-methionine with a particle size from 710 to 1000 micrometer, and
- up to 5 wt.-% of the D,L-methionine with a particle size of more than 1000 micrometer.

In another embodiment the D,L-methionine according to the present invention comprises up to 10 wt.-% of the D,L-methionine with a particle size in the range between 63 and 100 micrometer, from 20 to 50 wt.-% of the D,L-methionine with a particle size from more than 0 to less than 150 micrometer, from 50 to 70 wt.-% of the D,L-methionine with a particle size from more than 0 to less than 300 micrometer, from 30 to 65 wt.-% of the D,L-methionine with a particle size in the range between 63 and 300 micrometer, from 10 to 45 wt.-% of the D,L-methionine with a particle size in the range between 300 to 500 micrometer, from 1 to 20 wt.-% of the D,L-methionine with a particle size in the range between 500 to 710 micrometer, from more than 0 to 10 wt.-% of the D,L-methionine with a particle size from 710 to 1000 micrometer, and up to 5 wt.-% of the D,L-methionine with a particle size of more than 1000 micrometer.

D,L-Methionine with these features always has a bulk density of more than 710 kg/m³, specifically at least 720 kg/m³ or even up to more than 730 or 740 kg/m³.

In yet another embodiment the D,L-methionine according to the present invention comprises from 10 to 40 wt.-% of the D,L-methionine with a particle size from 300 to 500 micrometer.

In yet a further embodiment the D,L-methionine according to the present invention comprises up to 2 wt.-% of the D,L-methionine with a particle size of more than 1000 micrometer.

Preferably, the D,L-methionine according to the present invention comprises from 15 to less than 50 wt.-% of the D,L-methionine with a particle size from more than 0 to less than 150 micrometer, from 50 to 70 wt.-% of the D,L-methionine with a particle size of more than 0 to less than 300 micrometer, from 30 to 65 wt.-% of the D,L-methionine with a particle size in the range between 63 and 300 micrometer.

from more than 0 to 20 wt.-% of the D,L-methionine with a particle size of more than 0 to 32 micrometer, from more than 0 to 15 wt.-% of the D,L-methionine with a particle size in the range from 32 to 63 micrometer, from more than 0 to 10 wt.-% of the D,L-methionine with a particle size in the range from 63 to 100 micrometer, from 5 to 20 wt.-% of the D,L-methionine with a particle size in the range from 100 to 150 micrometer, from 5 to 20 wt.-% of the D,L-methionine with a particle size in the range from 150 to 200 micrometer, from 5 to 35 wt.-% of the D,L-methionine with a particle size in the range from 200 to 300 micrometer, from 10 to 45 wt.-% of the D,L-methionine with a particle size in the range from 300 to 500 micrometer, from more than 0 to 20 wt.-% of the D,L-methionine with a particle size in the range from 500 to 710 micrometer, from more than 0 to 10 wt.-% of the D,L-methionine with a particle size from 710 to 1000 micrometer up to 2 wt.-% of the D,L-methionine with a particle size of more than 1000 micrometer.

The present invention is not limited to a specific method regarding the determination of the individual weight percentages of the D,L-methionine with specific particle size. In the context of the present invention, it is preferred that the D,L-methionine with the whole spectrum of particle sizes is subjected to a sieving analysis, preferably to an aerodynamic sieve analysis according to the following method:

The whole spectrum of the particle size distribution of the D,L-methionine is determined using an air stream sieve machine, e.g. Type 200 LS-N from Hosokawa Alpine, with series of sieves of different mesh sizes (V2A-type). Said series of sieves starts with a sieve having a mesh size of more than 1000 µm, followed by a series of smaller and smaller mesh sizes (from 710 to 1000 µm, 500 to 710 µm, 300 to 500 µm, 200 to 300 µm, 150 to 200 µm, 100 to 150 µm, 63 to 100 µm, and 32 to 63 µm) and ends with a sieve having a mesh size of 32 µm at the most. The material is moved through the different sieves only by an air stream, so that any abrasions of the particles, which would influence the particle size distribution, can be neglected. In detail, a portion of the material to be analyzed, e.g. 25 g of the compound in question, is accurately weighed and placed onto the sieve with the finest mesh size. Said sieve is placed into the sieve machine, closed with a lid, and sieving is started. After a sieving time of 3 minutes the residue in the sieve is weighted, quantitatively transferred with a brush onto the sieve, which mesh size is next in size and the procedure is repeated. If electrostatic charging is a problem, 0.5 to 1% of an antistatic, e.g. alumina C, is added to the sample, based on the sample weight.

The sieve analysis is given as the percentage of the initial amount, which passed the sieve with the respective mesh size but remained on the sieve with the smaller mesh size. Said percentage can be calculated with the following formula:

$$\text{Residue} = \frac{R \times 100}{W}[\%]$$

where

W=weight of the sample in g, and

R=residue of the sample on the sieve with the respective mesh size in g.

The amount of the optionally added antistatic, e.g. alumina C, is so small that it can be neglected in the sieve analysis.

The bulk density is preferably determined according to DIN ISO 697 and EN ISO 60. For example, the following procedure may be used:

A standard equipment for determining bulk densities is used. Said equipment involves a tripod, which is equipped with a graduated cylinder, e.g. 250 ml, a funnel with a higher volume than the volume of the graduated cylinder and an outlet that is designed such that it flushes with the opening of the cylinder, a rotary damp, and a latch for the graduated cylinder. Before initial use, the height of the funnel has to be adapted to the graduated cylinder, and the rotary damp must be closed. Further, the weight of the unfilled graduated cylinder is weighted on a laboratory balance (type LP 4200 S from Sartorius) and then fixed in the standard equipment. Afterwards, the metallic funnel is completely filled with the substance to be tested. Before, the rotary damp is checked whether it is closed. Subsequently, the metallic funnel is filled completely with the substance to be tested, followed by opening the rotary damp so that the substance to be tested can easily flow into the graduated cylinder. Since the volume of the funnel is higher than the volume of the graduated cylinder, a slight overflow of the substance to be tested occurs. The slight overflow of the graduated cylinder is cut by completely closing the rotary damp and thus a constantly correct volume of 250 ml is achieved. Subsequently, the filled graduated cylinder is weighted on the laboratory balance. If necessary, a smooth cleaning of the outside of the graduated cylinder follows. The bulk density in kg/m³ can be calculated by multiplying the weight difference [g] with the necessary factor to reach a volume of 1000 ml, in case of the graduated cylinder with a volume of 250 ml said factor is 4. The general formula for the calculation of the bulk density is:

$$\text{Bulk density} = \frac{W \times 1000}{V_I} \left[\text{kg/m}^3\right]$$

where

W=weight of the sample in g, and $V_I$=initial volume in ml.

In principle, the present invention is not limited regarding a specific process for preparing the methionine according to the present invention. However, it was found that subjecting methionine to a pneumatic transport through a hollow spiral is particularly suitable for providing the methionine according to the present invention.

It is believed that due to the pneumatic transport the particles of the methionine are constantly moved, which leads to a collision of the particles with each other and also with the circular inner and outer walls of the hollow spiral. These collisions have an abrasive effect on the particles. The person skilled in the art should therefore expect that the pneumatic transport of methionine through a hollow spiral would lead to methionine with a large fraction or major part of very fine particles, specifically, with a large fraction of dust. Such a methionine would not have the suitable mix of fine, middle and coarse particles, which is beneficial for a high bulk density of methionine. It was therefore rather surprising that subjecting methionine to a pneumatic transport through a hollow spiral gives methionine with a suitable mix of fine, middle and coarse particles, which is beneficial for a high bulk density of methionine. The methionine obtained from a process for its preparation still contains moisture, in particular water, and is therefore hereinafter also referred to as moist methionine. It was found that the moisture can be removed from the methionine very efficiently by a convective transfer of heat from a heat medium to the methionine being transported through the hollow spiral. The said heat transfer and the pneumatic transport of methionine through the hollow spiral are therefore performed simultaneously.

Another object of the present invention is therefore a process for preparing the D,L-methionine according to the present invention, comprising the steps of i) pneumatically transporting D,L-methionine through a hollow spiral (1), and ii) convectively transferring heat from a heat exchange medium to the D,L-methionine being transported through the hollow spiral to remove moisture from the methionine, wherein the steps i) and ii) are performed simultaneously.

The process according to the present invention can be considered a post-treatment of D,L-methionine obtained from a process for its preparation. The The process for preparing the D,L-methionine according to the present invention is preferably integrated into the overall process for preparing methionine and is then part of the overall process for preparing methionine.

The term hollow spiral is used in the context of the present invention to denote a conveying unit, which can be represented by screw conveyor inside a tube, wherein the windings of the screw have a tight finishing with the tube. From the outside the hollow spiral looks like a tube with an opening and an outlet side at its opposite ends: the opening at its first end, where the methionine to be transported enters the hollow spiral, and the second opening at its other end, where the methionine to be transported exits the hollow spiral.

The term pneumatic transport or pneumatically transporting is used in the context of the present invention to denote a transportation of the methionine in step i) of the process by a gas stream, e.g. a stream of air. Accordingly, the pneumatic transport can be achieved by means of an excess pressure or pressure above atmospheric applied at the opening side of the hollow spiral, by which the methionine is pushed into and through the hollow sphere. An excess pressure or pressure above atmospheric is any type of pressure, which is higher than the atmospheric pressure. Alternatively, the pneumatic transported can also be achieved by applying a reduced pressure or sub-atmospheric pressure at the outlet side of the hollow spiral, by which the methionine is drawn or sucked into and through the hollow spiral. A reduced pressure or sub-atmospheric pressure is any type of pressure, which is lower than the atmospheric pressure. In any case, the excess pressure or the reduced pressure is the driving force, which pneumatically transports the methionine through the hollow spiral. In any case, it is therefore always necessary to establish a pressure difference between the opening and the outlet side of the hollow spiral, independently of whether an excess pressure or reduced pressure is used. For example, the pressure difference ranges from ca. 0.1 bar to ca. 10 bar, with individual pressure differences of 0.1, 1, 2, 3, 4, 5, 6, 7, 8, 9 or 10 bar. At standard operation conditions the preferred pressure difference is ca. 1 bar, 700 mbar or 600 mbar at the most.

In one embodiment the pneumatic transport in step i) of the process according to the present invention is achieved by excess pressure or reduced pressure. Preferably, the pneumatic transport in step i) of the process according to the present invention is achieved by excess pressure.

In the simplest case, the excess pressure is provided by means of a fan, and the reduced pressure is provided by means of a pump. Preferably, the fan or the pump have an upstream cyclone filter or cyclone separator, which separates any particles carried away from the surrounding, and thus holds them back from the gas stream, i.e. air stream.

The hollow spiral (1) also comprises a channel (2) running through the axis of said hollow spiral, which provides for the accommodation of a heat exchange medium. In addition, the hollow spiral (1) may also comprise a jacket (3) surrounding said hollow spiral, which also provides for the accommodation of a heat exchange medium. In any case, the heat transfer always occurs indirectly from the heat exchange medium to the methionine being pneumatically transported through the hollow spiral. Specifically, the heat transfer occurs by thermal conduction through a wall, which separates the hollow spiral from a jacket surrounding the hollow spiral, and/or by thermal conduction through a wall, which separates the hollow spiral from a channel inside the hollow spiral, which runs in the axis of said hollow spiral. Preferably, the hollow spiral (1) comprising the channel (2) running through the axis of said hollow spiral and the jacket (3) surrounding said hollow spiral, is a thin film dryer or swirl tube dryer.

According to this embodiment the heat transferred from a heat medium to the methionine removes moisture from the methionine. It is rather likely that the moist methionine subjected to this embodiment contains water because most process for the preparation of methionine involve an aqueous reaction medium or involve the re-crystallization from crude methionine in any aqueous medium. After being separated from the aqueous medium and optionally being subjected to a drying, the thus obtained methionine notwithstanding still contains residual moisture, which essentially is water. Therefore, a temperature of at least 100° C., e.g. between 110 and 140° C., is considered to be sufficient to remove water and any other solvents, in case methionine was prepared in a non-aqueous medium and/or re-crystallized from a non-aqueous medium, completely or at least as completely as possible form the methionine. In principle, this embodiment is not limited to any specific heat exchange media. Therefore, any type of heat exchange medium can be used, e.g. any type of fluids or mixture of fluids, for example a liquid, mixture of liquids, a gas, e.g. steam or hot vapor, or a mixture of gases, provided that said fluid or mixture of fluids has a sufficient heat capacity to store the required heat that is to be transferred to the methionine, specifically to transfer a heat of at least 100° C. to the methionine. The heat exchange medium is preferably fed through the channel (2) and the jacket (3), preferably in counter-current to the pneumatically transported methionine.

In a preferred embodiment of the process according to the present invention the heat exchange medium fed to step ii) has a temperature of at least 100° C.

In an embodiment of the process according to the present invention moist methionine is pneumatically transported through a hollow spiral (1), and simultaneously heat is convectively transferred from a heat exchange medium to the methionine being transported through the hollow spiral to remove moisture from the methionine. A high content of residual moisture in the methionine to be subjected to the present invention can have rather negative effects on the progress of the process or on the particle size distribution of the methionine. For example, a methionine, whose moisture content is too high, may clump together during the pneumatic transport through the hollow spiral. In the worst case this could lead to a clogging of the hollow spiral or a significantly less efficient heat transfer from the heat exchange medium to the methionine. This may lead to turbulences in the stream of pneumatically transported methionine, which is believed to lead to an excessive grinding of the methionine. This, however, would shift the particle size distribution of methionine towards smaller particles, i.e. finer particles oven more a larger fraction of dust particles than desired. The result would be a decrease in bulk density of methionine. It was found that methionine with a moisture content of up ca. 5 wt.-% can be still be fed to the process according to the present invention without either a clogging of the hollow spiral or any turbulences in the stream of pneumatically transported methionine or any other negative effects. The moisture content is determined after the methionine is separated from the mother liquor from which it was precipitated.

Therefore, in a preferred embodiment of the process according to the present invention the methionine fed to step i) has a moisture content of up to ca. 5 wt.-%.

Methionine with a moisture content of more than 5 wt.-% is mixed with dry methionine before being subjected to the process according to the present invention. The ratios in which the methionine with a moisture content of more than 5 wt.-% is mixed with dry methionine depend on the individual moisture content of the methionine.

The process according to the present invention allows the preparation of the D,L-methionine according to the present invention, including all embodiments mentioned above.

Another object of the present invention is therefore also the D,L-methionine according to present invention, which is obtained and/or obtainable by the process according to the present invention.

FIGURES

FIG. 1 is an exemplary representation of hollow spiral used in the process according to the present invention, wherein (1) is the hollow spiral including the channel (2) inside the hollow spiral, whose pathway is indicated by the light dotted line, and (3) is the jacket surrounding the hollow spiral.

EXAMPLES

1. Sieve Analysis

The particles size distribution of D,L-methionine was determined by aerodynamic sieve analysis using an air stream sieve machine, Type 200 LS-N from Hosokawa Alpine, with series of sieves of different mesh sizes (V2A-type). Said series of sieves started with a sieve having a mesh size of more than 1000 μm, followed by a series of smaller and smaller mesh sizes (from 710 to 1000 μm, 500 to 710 μm, 300 to 500 μm, 200 to 300 μm, 150 to 200 μm, 100 to 150 μm, 63 to 100 μm, and 32 to 63 μm) and ended with a sieve having a mesh size of 32 μm at the most. The material was moved through the different sieves only by an air stream, so that any abrasions of the particles, which would influence the particle size distribution, can be neglected. In detail, a portion of the material to be analyzed, e.g. 25 g of the compound in question, was accurately weighed and placed onto the sieve with the finest mesh size. Said sieve was placed into the sieve machine, closed with a lid, and sieving was started. After a sieving time of 3 minutes the residue in the sieve was weighted, quantitatively transferred with a brush onto the sieve, which mesh size is next in size and the procedure was repeated. If electrostatic charging was a problem, 0.5 to 1% of an antistatic, e.g. alumina C, based on the sample weight, was added to the sample.

The sieve analysis is given as the percentage of the initial amount, which passed the sieve with the respective mesh size but remained on the sieve with the smaller mesh size. Said percentage was calculated with the following formula:

$$\text{Residue} = \frac{R \times 100}{W} [\%]$$

with
   W=weight of the sample in g, and
   R=residue of the sample on the sieve with the respective mesh size in g.

2. Bulk Density

The bulk density of D,L-methionine was determined using the following procedure: A standard equipment for determining bulk densities was used. Said equipment involved a tripod, which was equipped with a graduated cylinder, e.g. 250 ml, a funnel with a higher volume than the volume of the graduated cylinder and an outlet that was designed such that it flushed with the opening of the cylinder, a rotary damp, and a latch for the graduated cylinder. Before initial use, the height of the funnel was adapted to the graduated cylinder, and the rotary damp was closed. Further, the weight of the unfilled graduated cylinder was weighted on a laboratory balance (type LP 4200 S from Sartorius) and then fixed in the standard equipment. Next, the rotary damp was checked whether it was closed. Subsequently, the metal- lic funnel was filled completely with the substance to be tested, followed by opening the rotary damp so that the substance to be tested could easily flow into the graduated cylinder. Since the volume of the funnel was higher than the volume of the graduated cylinder, a slight overflow of the substance to be tested occurred. The slight overflow of the graduated cylinder was cut by completely closing the rotary damp and thus a constantly correct volume of 250 ml was achieved. Subsequently, the filled graduated cylinder was weighted on the laboratory balance. If necessary, a smooth cleaning of the outside of the graduated cylinder followed. The bulk density in kg/m$^3$ was calculated by multiplying the weight difference [g] with the necessary factor to reach a volume of 1000 ml, in case of the graduated cylinder with a volume of 250 ml said factor was 4. The general formula for the calculation of the bulk density is:

$$\text{Bulk density} = \frac{W \times 1000}{V_I} \ [\text{kg/m}^3]$$

where
  W=weight of the sample in g, and
  $V_I$=initial volume in ml.

3. Comparative Example 1

In this example 3 runs of methionine crystals from two crystallizers were separated in a solid/liquid separation step from their mother liquor by means of a pump and vacuum belt filters. The thus obtained filter cake was washed and subjected to drying by stream treatment at the end of the belt filters. In detail, steam was directed at the filter cake from above in order to further dry out the filter cake by evapo- rating the mother liquor which usually remains in-between the crystals. The thus obtained methionine was subjected to sieve analysis and bulk density determination. The differ- ences in bulk density were due to varying crystallizer performances/operations. Table 1 gives the results of sieve analysis and bulk density determination, indicated as C1 to C3.

4. Example 1

The comparative example 1 was repeated with 10 runs with the exception that the D,L-methionine was subjected to a thin film dryer instead of a steam treatment. The thus obtained D,L-methionine was subjected to sieve analysis and bulk density determination. The differences in bulk density were due to varying crystallizer performances/op- erations and varying operating conditions of the thin film dryer. Table 1 gives the results of sieve analysis and bulk density determination, indicated as E1 to E10.

TABLE 1

| Example | 0-32 μm [wt.-%] | 32-63 μm [wt.-%] | 63-100 μm [wt.-%] | 100-150 μm [wt.-%] | 150-200 μm [wt.-%] | 200-300 μm [wt.-%] | 300-500 μm [wt.-%] | 500-710 μm [wt.-%] |
|---|---|---|---|---|---|---|---|---|
| C1 | 3.3 | 6.8 | 15.1 | 20.7 | 21 | 23.3 | 8.8 | 0.3 |
| C2 | 4.5 | 7.0 | 15 | 21.1 | 22 | 23 | 8.4 | 0.4 |
| C3 | 11.75 | 4.17 | 4.17 | 5.5 | 7.29 | 13.33 | 22.58 | 23.25 |
| E1 | 5.7 | 7.1 | 7.5 | 11.3 | 11.5 | 20.3 | 25.7 | 8.8 |
| E2 | 4.4 | 4.8 | 8.6 | 14.3 | 14.3 | 23.4 | 23.5 | 5.5 |
| E3 | 8 | 4.2 | 4.2 | 6.2 | 8 | 28.9 | 36.7 | 3.7 |
| E4 | 5.3 | 3 | 3.2 | 6.3 | 6.3 | 29.4 | 41.2 | 5.1 |
| E5 | 8.3 | 3.6 | 4.3 | 6.2 | 6.9 | 32.5 | 32.5 | 5.4 |
| E6 | 10.9 | 6.6 | 8.3 | 9.1 | 7.9 | 12.5 | 21.2 | 16.4 |
| E7 | 16.2 | 13.3 | 9 | 9.7 | 7.3 | 10.2 | 14.4 | 11 |
| E8 | 4.3 | 4 | 6 | 11.1 | 11.6 | 22.3 | 29.3 | 9.7 |
| E9 | 4 | 4.6 | 8.4 | 12.6 | 13.1 | 24.1 | 26.1 | 5.9 |
| E10 | 5 | 4.4 | 8 | 13.4 | 13.3 | 21.1 | 25.3 | 7.6 |

| Example | 710-1000 μm [wt.-%] | >1000 μm [wt.-%] | <63 μm [wt.-%] | <150 μm [wt.-%] | <300 μm [wt.-%] | 63-300 μm [wt.-%] | Bulk density [kg/m$^3$] |
|---|---|---|---|---|---|---|---|
| C1 | 0 | 0 | 10.1 | 45.9 | 90.2 | 80.1 | 695 |
| C2 | 0 | 0 | 11.5 | 47.6 | 92.6 | 81.1 | 700 |
| C3 | 6 | 2 | 15.92 | 25.59 | 46.21 | 30.29 | 650 |
| E1 | 2.0 | 0.3 | 12.8 | 31.6 | 63.4 | 50.6 | 715 |
| E2 | 1.1 | 0.1 | 9.2 | 32.1 | 69.8 | 60.6 | 720 |
| E3 | 0.4 | 0 | 12.2 | 22.6 | 59.6 | 47.3 | 720 |
| E4 | 0.3 | 0 | 8.3 | 17.8 | 53.5 | 45.2 | 720 |
| E5 | 0.4 | 0 | 11.9 | 22.4 | 61.8 | 49.9 | 731 |
| E6 | 6.9 | 0.3 | 17.5 | 34.9 | 55.3 | 37.8 | 738 |
| E7 | 7.9 | 1 | 29.5 | 48.2 | 65.7 | 36.2 | 744 |
| E8 | 2.1 | 0.2 | 8.3 | 25.4 | 59.3 | 51 | 748 |
| E9 | 1 | 0.1 | 8.6 | 29.6 | 66.8 | 58.2 | 751 |
| E10 | 1.7 | 0.1 | 9.4 | 30.8 | 65.2 | 55.8 | 753 |

The invention claimed is:

1. D,L-methionine, comprising, based on total D,L-methionine weight:

from 17.8 to less than 48.2 wt. % of first D,L-methionine particles with having a particle size of from more than 0 to less than 150 micrometers;

from 53.5 to less than 69.8 wt. % of second D,L-methionine particles with having a particle size from more than 0 to less than 300 micrometers; and from 30.29 to less than 60.6 wt. % of third D,L-methionine particles with having a particle size from 63 to 300 micrometers, from 4 to less than 16.2 wt. % of fourth D,L-methionine particles having a particle size from 0 to 32 micrometers;

from 3 to less than 13.3 wt. % of fifth D,L-methionine particles having a particle size from 32 to 63 micrometers;

from 3.2 to less than 9 wt. % of sixth D,L-methionine particles having a particle size from 63 to 100 micrometers;

from 6.2 to less than 14.3 wt. % of seventh D,L-methionine particles having a particle size from 100 to 150 micrometers;

from 6.3 to less than 14.3 wt. % of eighth D,L-methionine particles having a particle size from 150 to 200 micrometers;

from 10.2 to less than 32.5 wt. % of ninth D,L-methionine particles having a particle size from 200 to 300 micrometers;

from 14.4 to less than 41.2 wt. % of tenth D,L-methionine particles having a particle size from 300 to 500 micrometers;

from 3.7 to less than 16.4 wt. % of eleventh D,L-methionine particles having a particle size from 500 to 710 micrometers;

from 0.3 to less than 7.9 wt % of twelfth D,L-methionine particles having a particle size from 710 to 1000 micrometers;

from 0 to less than 0.3 wt. % of thirteenth D,L-methionine particles having a particle size of greater than 1000 micrometers;

from 8.3 to less than 29.5 wt % of fourteenth D,L-methionine particles having a particle size from 0 to 63 micrometers, and wherein the D,L-methionine has a bulk density of from 715 to 753 kg/m$^3$.

2. The D,L-methionine of claim 1, obtained by a process comprising:

(i) pneumatically transporting the D,L-methionine through a hollow spiral; and (ii) convectively transferring heat from a heat exchange medium to the D,L-methionine being transported through the hollow spiral to remove moisture from the D,L-methionine, wherein the pneumatically transporting (i) and convectively transferring (ii) are performed simultaneously.

3. A process for preparing the D,L-methionine of claim 1, the process comprising:

(i) pneumatically transporting the D,L-methionine through a hollow spiral; and (ii) convectively transferring heat from a heat exchange medium to the D,L-methionine being transported through the hollow spiral to remove moisture from the D,L-methionine, wherein the pneumatically transporting (i) and convectively transferring (ii) are performed simultaneously, and wherein a pressure difference of at most 700 mbar is applied to the hollow spiral.

4. The process of claim 3, wherein the pressure difference of at most 600 mbar is applied to the hollow spiral.

* * * * *